United States Patent [19]

Tsai et al.

[11] Patent Number: 4,719,272

[45] Date of Patent: Jan. 12, 1988

[54] MONOMERIC CATIONIC GLYCOSIDE DERIVATIVES

[75] Inventors: John J. Tsai, Belle Mead; Martin M. Tessler, Edison, both of N.J.

[73] Assignee: National Starch and Chemical Corporation, Bridgewater, N.J.

[21] Appl. No.: 11,170

[22] Filed: Feb. 5, 1987

Related U.S. Application Data

[63] Continuation-in-part of Ser. No. 625,289, Jun. 27, 1984, abandoned.

[51] Int. Cl.$^4$ .............................................. C08F 10/00
[52] U.S. Cl. .......................... 526/238.2; 526/238.21; 526/238.22; 526/238.23; 536/4.1; 536/17.3; 536/17.4; 536/17.9
[58] Field of Search ........... 526/238.2, 238.21, 238.22, 526/238.23; 536/4.1, 17.3, 17.4, 17.9, 120

[56] References Cited

U.S. PATENT DOCUMENTS

| | | | |
|---|---|---|---|
| 3,356,652 | 12/1967 | Chaudhuri | 260/78.4 |
| 3,931,148 | 1/1976 | Langdon | 260/210 |
| 4,328,337 | 5/1982 | Kawasaki | 536/119 |

FOREIGN PATENT DOCUMENTS 625624  7/1949  United Kingdom.

Primary Examiner—Joseph L. Schofer
Assistant Examiner—Alex H. Walker
Attorney, Agent, or Firm—Edwin M. Szala; Lori D. Tolly

[57] ABSTRACT

Novel cationic unsaturated mono- and polysaccharide glycoside derivatives are prepared by reacting glycidyl, halohydrin or haloalkyl glycosides (e.g. 3-chloro-2-hydroxypropyl glucoglycoside) with unsaturated amines (e.g. N,N-dimethylaminopropyl methacrylamide). The novel monomers may be homo- or copolymerized in order to prepare novel cationic polymers with pendant saccharide side chains. The monomers may also be used in the preparation of cationic polysaccharide graft copolymers.

16 Claims, No Drawings

MONOMERIC CATIONIC GLYCOSIDE DERIVATIVES

This is a continuation-in-part of Ser. No. 625,289, filed on June 27, 1984, now abandoned.

BACKGROUND OF THE INVENTION

This invention relates to cationic unsaturated mono- and polysaccharide glycoside derivatives, as well as to the polymers derived therefrom.

Ethylenically unsaturated mono- and disaccharide glycoside derivatives as well as homo- and copolymers derived therefrom have been prepared. See, for example, U.S. Pat. No. 3,356,652 issued on Dec. 5, 1967 to D. Ray-Chaudhuri which describes the preparation of a glycoside containing an ethylenically unsaturated sidechain linked to the number 1 carbon of a 2,3,4,6-tetra-O-acetylglucose molecule by reacting a tetraacetylglycosyl halide with a monohydroxy or monocarboxy ethylenically unsaturated monomer. The homo- and copolymers prepared from the acetylated glycosidic monomers are soluble in organic solvents. Upon deacetylation, the homo- and copolymers having a mole fraction of at least 20% of the glucoside derivatives become readily water soluble with a greater hydrophilic character than other commonly available synthetic water soluble polymers. The polymers are described as having broad utility in the adhesive, textile, and paper industries.

Similarly, U.S. Pat. No. 4,328,337 issued May 4, 1982 to T. Kawasaki et al. describes the preparation of high polymeric substances having repeating mono- or disaccharide side chains prepared by homopolymerizing (meth)acroyl mono- or disaccharide glycosides. These high polymers are described as being water soluble with excellent bio-adaptability and having a membrane-forming property. When cross-linked, the homopolymers have a high water-retaining property which is useful for many medical treatments.

In U.S. Pat. No. 3,931,148 issued on Jan. 6, 1976 to W. Langdon, novel neutral and cationic glycosidic surfactants are prepared by reacting a 2-hydroxy-3-chloropropyl glycoside of a mono- or polysaccharide with an alkyl amine which contains at least one hydrophobic $C_8$-$C_{18}$ alkyl group. The alkyl amines are described as having 8-30 carbon atoms which may be primary, secondary, tertiary, aliphatic, saturated or unsaturated, alicyclic and aralkyl. The glycosides are described as being useful in areas requiring surfactants exhibiting biodegradability, alkali solubility and stability.

Due to the low cost and abundance of many saccharides in addition to the hydrophilic nature they provide to polymers, it is the prime objective of this invention to produce a novel class of cationic unsaturated mono- and polysaccharide glycoside derivatives, the derivatives being capable of undergoing homopolymerization or copolymerization in the presence of other unsaturated comonomers. None of the above references disclose or suggest the products of the present invention.

SUMMARY

Novel cationic unsaturated mono- and polysaccharide glycoside derivatives are provided which have the following structure:

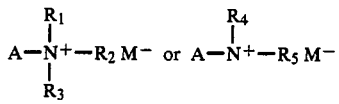

wherein A is $(saccharide)_n$—O—B and $(saccharide)_n$—O— represents a mono- or polysaccharide where O is attached to the glycosidic carbon atom in the terminal saccharide ring of $(saccharide)_n$, B is —$CH_2CH(OH)CH_2$— or —$CH_2CH_2$—, and n is 1 to 20;

wherein $R_1$ may be H; $C_1$-$C_6$ alkyl; $C_2$-$C_6$ alkenyl or alkynyl; benzyl; or A;

$R_2$ may be H; $C_1$-$C_6$ alkyl; $C_2$-$C_6$ alkenyl or alkynyl; benzyl; or A;

$R_3$ may be $C_2$-$C_7$ alkenyl or alkynyl or represented by the formula —Z—C[Y]=$CH_2$ or —Z—C≡CH wherein Z is a divalent organo group containing a polar activating group and Y is H or $C_1$-$C_3$ alkyl; or wherein $R_2$ and $R_3$ together with the nitrogen atom to which they are bonded may form optionally a 5 or 6 member saturated heterocyclic ring substituted with a group represented by the formula —C[Y]=$CH_2$ or —C≡CH;

wherein $R_4$ and $R_5$ together with the nitrogen atom to which they are bonded optionally form a 5 or 6 member unsaturated heterocyclic ring substituted with a group represented by the formula —C[Y]=$CH_2$ or —C≡CH; and wherein M is an anion.

The derivatives may be homopolymerized or copolymerized to produce novel cationic polymers having pendant saccharide side chains which are useful as flocculants and in papermaking. Useful graft copolymers of the cationic monomers to a polysaccharide may also be prepared.

DETAILED DESCRIPTION OF THE PREFERRED EMBODIMENTS

Glycosides may be prepared from mono- and polysaccharides which contain a reducing carbon atom. This carbon atom, which is located in the terminal saccharide ring, is capable of reacting with alcohol to form glycosidic products attached by an acetal or ketal linkage, depending on the mono- or polysaccharide employed.

One class of glycosides which are applicable for use as intermediates in preparing the novel monomeric derivatives herein include halohydrin or glycidyl glycosides having the general formula:

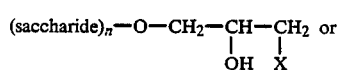

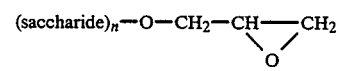

wherein $(saccharide)_n$—O— represents a mono- or polysaccharide where O is attached to the glycosidic carbon atom in the terminal saccharide ring of $(saccharide)_n$, X is chlorine or bromine, and n is 1 to 20.

W. Langdon (discussed above) prepares similar glycosides by reacting monosaccharides and polysaccharides which are hydrolysable to monosaccharides (including starch and cellulose) at temperatures of about 94° to 108° C. with 3-chloro-1,2-propandiol in the presence of about 0.01 to 2.0 weight percent, based on the reactants, of a strong acid catalyst. The procedure produces severely hydrolyzed products in poor yields which are a dark color, probably due to charring caused by the acid at such high reaction temperatures.

We prefer to prepare the glycosides by reacting a mono- or polysaccharide in an excess of 3-halo-1,2-propandiol in the presence of a cation exchange resin. By employing a cation exchange resin, mono- and polysaccharide glycosides may be prepared at moderate temperatures without charring and with only minimal degradation occurring. Additionally, no neutralization step is required as in acid catalyzed systems as the catalyst may be easily removed by filtration.

The reaction is conducted with stirring at a temperature of about 55°–80° C., preferably 60°–65° C. over a period of about 3–20 hours, preferably 6–8 hours. By employing the preferred lower temperatures and shortened reaction times, the amount of oligosaccharide formation and polysaccharide degradation is reduced. After the reaction is complete, the mixture is filtered in order to remove the cation exchange resin. The excess diol may then be removed by a number of methods including, for example, vacuum distillation or washing with organic solvents in order to obtain the 3-halo-2-hydroxypropyl glycoside. When monosaccharide glycoside reagents are prepared, the diol may be removed from the glycoside by vacuum distillation, preferably at a temperature of about 80° C. and a pressure of 2 mm Hg. or lower temperatures and pressures. After distillation, the glycoside may optionally be washed with an organic solvent such as acetone or ethyl acetate. Glycosides prepared with polysaccharides may be purified by vacuum distillation, however distillation temperatures above about 60° C. may cause some degradation. These glycosides are preferably recovered by suspending the glycoside/diol mixture in an organic solvent and filtering a number of times to remove the excess diol and other impurities.

The glycidyl glycosides useful herein may be prepared by reacting a 3-halo-2-hydroxypropyl glycoside with an alkali metal hydroxide in order to form the epoxide group. Typically, the glycoside is mixed with an aqueous alkaline solution while cooling. The mixture is neutralized with acid and then dissolved in alcohol in order to precipitate the metal salts formed. After filtration, the glycidyl glycoside may be recovered by removing the alcohol and water by vacuum distillation.

The monosaccharides which may be employed in the preparation of the glycoside reagent include glucose, fructose, sorbose, mannose, galactose, talose, allose, altrose, gulose, idose, arabinose, xylose, lyxose, ribose, and other similar monosaccharides. Polysaccharides which may be employed in the preparation of the glycosides include maltose, gentiobiose, lactose, cellobiose, maltodextrins of starch having a dextrose equivalent (D.E.) of 5 or greater and other similar polysaccharides comprising no more than about 20 saccharide units.

The halogenated propanediols which may be employed include 3-chloro-1,2-propandiol and 3-bromo-1,2-propandiol. The use of the chloro derivative is preferred due to its commercial availability and cost. The particular saccharide employed and its degree of solubility in the halogenated propanediol will determine the minimum amount of reagent required. While a saccharide to diol ratio of as little as 1:1.4 has been employed, a preferred ratio is at least 1:3 to 1:6, most preferably 1:5. As described above, monosaccharides and polysaccharides of up to about 20 saccharide units which contain a reducing carbon atom are applicable herein. It was found that as the number of saccharide units increases the polysaccharide becomes less reactive and more difficult to dissolve in the 3-halo-1,2-propandiol without employing undesirably high temperatures which cause significant degradation.

Any cation exchange resin may be used in the glycoside preparation. Suitable exchange resins include sulfonated-crosslinked polystyrene such as commercially available Amberlite IR-120 from Rohm and Haas, Dowex 50 from Dow Chemical and Permutit Q from Permutit; sulfonated phenolics such as Duolite C-3 from Diamond Shamrock; and sulfonated coals such as Zeo Karb H from Permutit. The preferred cation exchange resin is Dowex 50. The amount of resin useful herein is about 1 part resin to 2–8 parts by weight of saccharide, preferably 1 part resin to 4–5 parts saccharide.

Another class of glycosides which are useful as intermediates in preparing the monomers herein include haloethyl glycoside reagents having the formula:

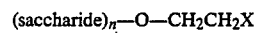

(saccharide)$_n$—O—CH$_2$CH$_2$X wherein (saccharide)$_n$—O— and X have the meanings described above. The haloethyl glycoside reagents may be prepared by similar methods described above employing the desired saccharide and haloethanol.

The novel cationic glycoside monomers of the presention invention are represented by the following structures:

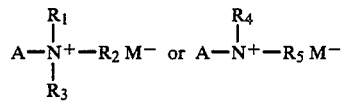

$$A-\overset{R_1}{\underset{R_3}{N^+}}-R_2\ M^-\ \text{or}\ A-N^+-R_5\ M^-$$

wherein A, R$_1$, R$_2$, R$_3$, R$_4$, and R$_5$ have the meanings described above. M is an anion, such as a halogen ion (chloride, bromide, or iodide), or the anion of any other acid, such as nitrate, phosphate, acid phosphate, sulfate, bisulfate, methyl sulfate, carboxylate, sulfonate, sulfamate, acetate, formate, oxylate, acrylate and α-methacryloxyacetate. In the case where the anion is polyvalent, of course, the number of anions present is inversely proportional to the valency. The chloride ion is normally the most convenient.

In the process of preparing the novel monomeric cationic glycoside derivatives, the halohydrin, glycidyl, or haloethyl glycoside is reacted with an unsaturated amine represented by the formula:

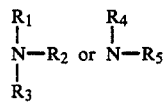

$$\overset{R_1}{\underset{R_3}{N}}-R_2\ \text{or}\ \overset{R_4}{N}-R_5$$

wherein

R$_1$ may be H; C$_1$–C$_6$ alkyl; C$_2$–C$_6$ alkenyl or alkynyl; or benzyl;

R$_2$ may be H; C$_1$–C$_6$ alkyl; C$_2$–C$_6$ alkenyl or alkynyl; or benzyl;

R$_3$ may be C$_2$–C$_7$ alkenyl or alkynyl or represented by the formula —Z—C[Y]=CH$_2$ or —Z—C≡CH wherein Z is a divalent organo group containing a polar activating group and Y is H or C$_1$–C$_3$ alkyl; or wherein R$_2$ and R$_3$ together with the nitrogen atom to which they are bonded may form optionally a 5 or 6 member saturated heterocyclic ring substituted with a group represented by the formula —C[Y]=CH$_2$ or —C≡CH; and wherein R$_4$ and R$_5$ together with the nitrogen atom to which they are bonded optionally form a 5 or 6 member unsaturated heterocyclic ring substituted with a group represented by the formula —C[Y]=CH$_2$ or —C≡CH. The heterocyclic rings will generally comprise at least two carbon atoms with the remaining ring constituents selected from such atoms, for example, as oxygen, nitrogen, sulfur, and phosphorus. Among the amines which are applicable for use in this process, one may list, for example:

N,N-dimethylaminopropyl(meth)acrylamide
N,N-diethylaminopropyl(meth)acrylamide
N,N-dipropylaminopropyl(meth)acrylamide
N,N-dimethylaminopropyl(meth)acrylate
N,N-diethylaminopropyl(meth)acrylate
N,N-dipropylaminopropyl(meth)acrylate
N,N-dimethylaminoethyl(meth)acrylate
N,N-dipropylaminoethyl(meth)acrylate
N,N-dibutylaminoethyl(meth)acrylate
N,N-diisopropylaminoethyl(meth)acrylate
N-methyl diallyl amine
triallyl amine
vinyl pyridine
vinyl pyrrole
vinyl imidazole
N-methyl vinyl pyrrolidine
N-methyl vinyl piperidine
N-methyl vinyl piperazine The steric configuration, polarity, and the position of the unsaturation will affect the polymerizability of the novel cationic glycoside monomers produced. Monomers containing polar groups juxtapositional to the unsaturated bond which activate bond in the presence of free-radical initiating systems will polymerize more readily than monomers which do not contain such polar groups. Monomers containing polar groups which are not juxtapositional to the unsaturated bond and as such will not activate the bond are also not as reactive. Illustrative activating polar groups include

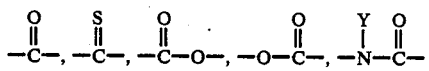

groups and the like. Amines represented by the formula

wherein R$_1$ and R$_2$ are described above, R$_3$ is —Z—C-[Y]=CH$_2$ wherein Y is described above and Z is —Q—P— which represents a divalent organo group containing a polar activating group (P) juxtapositional to the unsaturated group and Q is an alkyl group (e.g., C$_1$-C$_6$), are preferably employed in the preparation of the novel glycoside monomers.

The halohydrin or glycidyl glycoside reagents may be used interchangeably in the preparation of the novel monomers herein as these glycosides will only react with the amines under alkaline conditions after the halohydrin is first converted to the epoxide form. It should be noted that the amines employed will generally provide sufficient alkalinity to allow the reaction to proceed without the need for additional base. For this reason, the use of the halohydrin glycoside reagent is preferred.

The unsaturated amine selected and the final glycosidic monomer desired will determine the necessary glycoside to amine molar ratio to be employed. When reacting an amine with the glycosidic reagent, generally an equimolar concentration or a concentration of amine amounting to a slight stoichiometric excess in the order of about 10 to 20% of the glycoside is employed. When reacting with a primary amine, one, two or more molar equivalents of glycoside may be employed. It should be understood that steric hinderance may be a factor as to whether di- or triglycoside monomers may be produced.

In conducting the process of this invention, the selected unsaturated amine is first slowly added to an aqueous solution of the glycoside reagent. During the addition, the reaction mixture is cooled in order to maintain a temperature below about 60° C. The reaction is then conducted, ordinarily in the presence of a polymerization inhibitor, with stirring at a temperature of about 25° to 65° C., preferably 35°-42° C. over a period of about 6 to 24 hours, preferably 12 to 16 hours. At the higher reaction temperatures, a polymerization inhibitor such as monoethyl ether hydroquinone should be employed. After the reaction is complete, the solution is concentrated by removal of the water by vacuum distillation after which the novel monomer may optionally be washed with an organic solvent such as acetone. While water is the preferred reaction medium of choice, it should be noted that other polar solvents such as, for example, N-methyl-pyrrolidinone may be employed.

In general, the novel monomers of this invention are hygroscopic syrups or tacky solids depending on the saccharide length of the glycoside reagent employed. When employing tertiary or secondary amines, the cationic glycoside monomers prepared by the above described process are produced in or near quantitative yields. In the case of reactions of primary amines with stoichiometric amounts of glycoside reagent the resultant yields of cationic monomer may be less than quantitative.

In utilizing our cationic unsaturated glycoside derivatives in the preparation of homo- and copolymers, there may be employed any of the usual vinyl polymerization methods which are well known to those skilled in the art and which are particularly suited for the homo- or copolymer whose preparation is desired. Thus, such polymers may be prepared by means of free radical initiated processes utilizing bulk, suspension, solution, or emulsion polymerization techniques.

We preferably prepare the polymers in water-in-oil self-inverting emulsion form by the processes described in U.S. Pat. Nos. 3,284,393 (issued Nov. 8, 1966 to J. Vanderhoff et al.), 4,022,736 (issued May 10, 1977 to J. Schmitt), 4,077,930 (issued Mar. 7, 1978 to S. K. Lim et al.) and 4,363,886 (issued Dec. 14, 1982 to S. Lipowski et al.). In the process, an aqueous solution of the cationic unsaturated glycoside monomer is mixed with rapid agitation with a hydrophobic liquid and water-in-oil emulsifying agents to form an emulsion then polymerized in the presence of a free radical polymerization catalyst.

The comonomers which may be utilized together with the above described cationic unsaturated glycoside monomers for the preparation of the polymers of our invention can be any unsaturated monomer polymerizable therewith such, for example, as styrene and substituted styrenes, e.g., alpha-methyl styrene; acrylic acid, alkyl and hydroxyalkyl substituted acrylic acids, the alkali metal, alkaline earth metal, and ammonium salts thereof, and the esters thereof with $C_1$-$C_{18}$ alcohols, e.g., methyl, ethyl, propyl, butyl, isobutyl, amyl, hexyl, octyl, lauryl and stearyl alcohols; the dialkylaminoalkyl esters of acrylic and methacrylic acids; isoprene; acrylamide and lower alkyl substituted acrylamides, the N-alkyl substituted and N-alkanol substituted compounds thereof; acrylonitrile; methacrylonitrile; butadiene; vinyl compounds, e.g., vinyl pyrrolidone, acetate, propionate, formate, etc.; halogenated vinyl compounds, e.g., vinylidene chloride, vinyl chloride, vinyl fluoride, etc.; unsaturated vinylic acids, e.g., maleic acid or anhydride, itaconic acid, etc., and salts thereof; esters of vinylic acids, e.g., dibutyl fumarate and maleate; (meth)allyl esters of saturated aliphatic monocarboxylic acids, such as (meth)allyl acetates, propionates, and valerates; ethylene; and propylene. Any of these comonomers may be used either alone or in combination with one another together with one or more of our cationic monomers. Minor amounts of crosslinking monomers such as diallyl maleate and diallyl phthalate may also be employed.

The polymeric substances of the present invention include those having a synthetic polymer backbone which contain recurring saccharide side chain units represented by the formula:

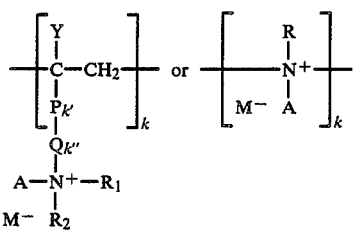

wherein
R is H or methyl;
$R_1$ and $R_2$ are independently H, $C_1$-$C_6$ alkyl, benzyl, or A;
k' and k" are independently 0 or 1 with the proviso that k'+k">0;
k is an integer greater than 1, preferably 2 to 1000; and
A, P, Q, Y, and M have the meanings previously given.

While the polymeric substances represented by the above formula have been described as the homo- and copolymerization products of the present cationic glycosidic monomers, it will also be understood that similar products may be obtained by the reaction under alkaline conditions of a halohydrin, glycidyl, or haloethyl glycoside reagent described above with a polymer containing reactive amine groups (e.g., such as polymers of dimethylaminopropyl methacrylamide).

The cationic glycosidic monomers of the present invention may also be employed in the preparation of novel cationic graft copolymers of polysaccharides.

The polysaccharide substrates suitable for use in the practice of this invention include starches and starch conversion products derived from any plant source; starch ethers and esters; cellulose and cellulose derivatives and various plant gums (e.g., guar gum). The substrate may be used in water soluble or water insoluble form.

Starches including those derived from corn, potato, wheat, rice, sago, tapioca, waxy maize, and sorghum, and amylose, as well as the conversion products and derivatives thereof, are the preferred substrates due to their cost and availability.

The term polysaccharide graft copolymers or "Polysacch-g-copolymer" as used herein refers to a polysaccharide base having copolymeric side chains grafted onto the hydroxyl groups of the polysaccharide molecule wherein the grafted side chains, straight or branched, are polymers of the cationic glycoside monomers of the present invention. The polymeric side chains are added to the polysaccharide base by polymerization of the unsaturated monomer. The graft copolymers also encompass those prepared from polysaccharide derivatives containing unsaturated substituents (e.g., 3-allyloxy-2-hydroxypropyl starch ether).

Methods for preparing graft copolymers of polysaccharides such as starches, cellulose and gums are well known in the literature. See, for example, "Block and Graft Copolymerization", Vol. 1, R. J. Ceresa, ed., John Wiley and Sons (1973). Such methods, as represented by the teachings of U.S. Pat. Nos. 3,809,664 and 3,976,552 (issued May 7, 1974 and Aug. 24, 1976, respectively to Fanta et al.) include polymerizations in water, in water-solvent mixtures and in the dry state, and may be initiated by mechanical, chemical and irradiative techniques. A preferred method of preparation is described in U.S. Pat. No. 4,131,576 (issued Dec. 26, 1978 to C. Iovine et al.), the disclosure of which is incorporated herein by reference.

The cationic glycoside monomer described herein may be used as the sole component of the polysaccharide graft or may be used as a comonomer with another copolymerizable comonomer suitable for graft copolymerization. Suitable comonomers with the cationic glycoside monomers are described above. Preferred comonomers include acrylic acid, substituted acrylic acids, and the esters thereof; acrylamide and substituted acrylamides; styrene and substituted styrenes; and vinyl compounds.

In practice, from about 1 to 100% of the cationic glycoside monomer, based on dry polysaccharide, may be used in the polymerization depending on the polysaccharide base used, the monomer(s) employed, the degree of grafting desired and the reaction conditions employed.

The cationic polysaccharide graft copolymers herein may be represented by the structure:

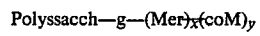

wherein Polysacch represents a polysaccharide molecule; Mer represents the cationic glycoside monomer having the structure:

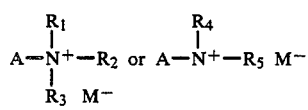

wherein A, $R_1$-$R_5$, and M have the meanings given above, coM represents a copolymerizable comonomer; and x and y are integers wherein x is at least 1 and x+y≦2.

The practitioner will recognize that the final structure of the resulting polysaccharide-g-copolymers cannot be predicted since branching is possible when the monomers employed contain more than one polymerizable group. Also, depending on the reactivity of the monomers employed, one may obtain random, block, or alternating grafts. The practioner will also recognize that a polysaccharide molecule is a polymer which contains many anhydro sugar units, each having on the average three free hydroxyl groups which may reaction with different reactivities with the monomers depending on such factors as the particular polysaccharide employed, the ratio of polysaccharide to monomer employed and, to some extent, the reaction conditions.

Many cationic polymers are employed as flocculants for aiding the separation of finely divided particles, such for example, as minerals from aqueous suspension. The rate of flocculation is known to behave as a function of the charge number, molecular weight, and molecular structure of the polymer employed. While the novel cationic glycoside monomers herein do not flocculate clay suspensions, many of the cationic homopolymers, copolymers and polysaccharide graft copolymers described herein do provide good to excellent clay flocculation times. In papermaking, the ease with which water drains from stock on a paper machine "wire" and amount of water retained in the wet web as it passes to and through the presses affects both speed of the machine and quality of the paper. Use of the cationic homo- and copolymers as well as the amphoteric copolymers herein as drainage aids was seen to improve drainage rates. The polymers may also find use as pigment or strength retention aids in papermaking. The following test procedures were used to evaluate the polymers described herein:

CLAY FLOCCULATON TEST

A total of 38 parts Attasorb clay (obtained from Englehard Industries, Inc.) and 3462 parts water are stirred for 16 hours at room temperature. A portion of this clay suspension is added to fill a 1000 ml graduated cylinder then mixed with a plunger three times. A total of 40 ml. of a 0.1% polymer solution is then added to the clay suspension and again plunged three times. The clay flocculation time is recorded as the number of seconds necessary for the 40 ppm polymer treatment to cause the clay to flocculate and settle to the 700 ml mark of the graduated cylinder. A cationic diethylaminoethyl ether corn starch derivative useful as a clay flocculant (described in U.S. Pat. No. 2,813,093 issued on Nov. 12, 1957 to C. Caldwell et al.) which has a clay flocculation time of 70 seconds was used for comparison.

EVALUATION AS DRAINAGE AIDS

Unbleached soft wood kraft pulp at a 1.5% consistency is beaten in a Valley Beater to approximately 600 C.S.F. (Canadian Standard Freeness). The pulp stock is then aged for two days under ambient air temperature (18°-24° C.). The pulp is diluted with water to obtain a 0.5% consistency then neutralized to 7.0 pH with sulfuric acid. This pulp stock is used for the drainage test in a neutral system. For the drainage test in an acid system, alum (approximately 3.3% on dry pulp basis) of the polymers is added at treatment levels of 0.1 to 0.5% on dry pulp basis to a 345 ml aliquot of either the neutral or acid pulp stock. After mixing for one minute, the treated pulp stock is added to a graduated dynamic drainage cylinder containing 1553 ml of 100 ppm $CaCO_3$ water which has a marine type propeller positioned at the 500 ml mark. A predetermined drainage volume of 1200 ml was chosen. After the pulp slurry is mixed for 30 seconds, the stopper at the bottom of the cylinder is pulled. When the pulp stock volume is drained to the 1500 ml mark, the seconds timer is started. After the volume is drained to the 300 ml cylinder mark, the timer is stopped. A sample's drainage rate is measured in ml/sec with the best drainage aid having the fastest drainage rate.

The control for the drainage test in a neutral system consisted of a cationic starch ether derivative of the prior art, i.e. the diethylaminoethyl ether of waxy maize containing 0.27% nitrogen by weight (dry basis). The control for the acid system consisted of an amphoteric starch ether derivative of the prior art, i.e. the phosphorylated diethylaminoethyl ether of waxy maize containing 0.27% nitrogen and 0.1% phosphorus by weight (dry basis). Both starch derivatives were prepared as described in U.S. Pat. No. 3,459,632 issued on Aug. 5, 1969 to C. G. Caldwell et al.

The following examples will more fully illustrate the practice of this invention but they are not intended to limit its scope. In the examples, all parts and percentages are given by weight and all temperatures are in degrees Celsius unless otherwise noted.

EXAMPLE 1

This example illustrates the preparation of 3-chloro-2-hydroxypropyl glucoglycoside.

To a 0.5 liter round-bottom flask equipped with condenser, mechanical stirrer and means for heating, there was added 80 g. (0.44 mole) of dextrose, 237 g. (2.15 moles) of 3-chloro-1,2-propandiol, and 20 g. Dowex 50W-X8 cation exchange resin (4.83 meq/g) in H+ form. The mixture was heated to 60° C. and stirred at that temperature for 16 hours. The reaction mixture was cooled and then filtered over a guaze cloth to remove the resin. The reaction mixture was clear and light yellow in color. Unreacted diol was removed by vacuum distillation at 80° C. at 2 mm Hg. The hygroscopic solid product was slurried in acetone and filtered three times to remove residual impurities then dried in a vacuum dessicator. The light beige colored glycoside was removed in an 80% yield (based on theoretical). $C^{13}$ NMR spectral analysis indicated the absence of the reducing carbon atom hemi-acetal signals at 92 and 96 ppm. Signals were recorded indicating a glycosidic carbon at 100.2 and 104.3 ppm corresponding to an acetal linkage. Organic chlorine analysis showed the glycoside to contain 11.5% organic chlorine instead of the expected value of 13.02% based on a 272.54 molecular weight of the glycoside. This indicates that a small degree of oligosaccharide formation occurred resulting in a product containing both the glucoglycoside as well as a small amount of oligosaccharide glycoside.

EXAMPLE 2

This example illustrates the preparation of the 3-chloro-2-hydroxypropyl glycoside of a maltodextrin containing ten glucose units connected by either 1,4 or 1,6 linkages, referred to as having a D.E. of 10.

The procedure of Example 1 was followed except that the reaction time was reduced to 6 hours and the vacuum distillation step was omitted. The maltodextrin glycoside was recovered in an 84% yield (based on theoretical). The $C^{13}$ NMR spectra of the glycoside product revealed no signals corresponding to the hemi-acetal form of the reducing carbon atom of the maltodextrin. Signals were recorded at 98.6, 99.9, and 102.8 ppm corresponding to the α- and β-glycoside carbon linkages of the maltodextrin. Analysis showed the organic chlorine content of the product to be 2.62% as compared to an expected 2.15% based on the molecular weight of the D.E. 10 glycoside. This indicates the presence of some lower molecular weight chlorohydrin glycoside present caused by slight degradation.

EXAMPLE 3

This example illustrates the preparation of N-[2-hydroxy-3-glucoglycosylpropyl], N,N-dimethyl, 3-methacrylamidopropylammonium chloride.

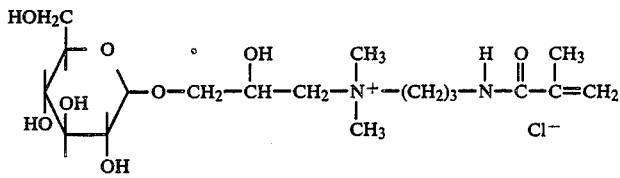

A total of 35.3 grams dry basis (0.13 moles) of 3-chloro-2-hydroxypropyl glucoglycoside of Example 1 was dissolved in 30 ml of distilled water in a 250 ml. round bottom flask. While cooling in an ice bath, 22.1 grams (0.13 moles) of N,N-dimethylaminopropyl methacrylamide was added slowly over a period of 30 minutes with an addition funnel. Five drops of a 1% monomethyl ether hydroquinone ethanol solution were added then the reaction mixture was heated to 40° C. with stirring for 16 hours. The mixture was concentrated on a rotary evaporator at 40° C., extracted with acetone to remove any unreacted vinyl monomer then dried in a vacuum dessicator. The desired product, which will for purposes of brevity be hereinafter referred to as DMAPMA-glucoglycoside (MW~443), was a yellow syrup.

No organic chloride was detected by chlorine analysis indicating the reaction was quantitative. IR analysis showed signals at 1605 and 1670 cm$^{-1}$ indicating the presence of the acryloyl functionality. C$^{13}$ NMR spectral analysis showed no reducing glycosidic carbon present but acryloyl carbon atoms signals were picked up at 172.4, 139.4, and 122.0 ppm.

EXAMPLE 4

This example illustrates the preparation of DMAPMA-glucoglycoside employing N-methyl pyrolidinone as a reaction medium.

Employing the reaction conditions of Example 3, 17.0 g dry basis (0.062 moles) of 3-chloro-2-hydroxypropyl glucoglycoside of Example 1 was dissolved in 10 ml of N-methyl pyrrolidinone and reacted with 10.81 g (0.063 moles) of N,N-dimethylaminopropyl methacrylamide in the presence of 2 drops of 1% monomethyl ether hydroquinone ethanol solution and 8 drops of 2,4,6-trimethylpyridine. The reaction was conducted at a temperature of 60° C. for 16 hours then cooled to room temperature. The DMAPMA-glucoglycoside was recovered by precipitation in acetone and dried in a vacuum dessicator. Based on organic chloride concentration, the glycoside monomer was prepared in about 52% yield based on theoretical, indicating that water is a preferred reaction medium for the monomer preparation.

EXAMPLE 5

Instead of the glucoglycoside, the maltodextrin 10 glycoside of Example 2 was employed in the reaction of Example 3 to obtain a slightly yellow, tacky semi-solid in a quantitative yield based on organic chlorine analysis. According to the results of IR and C$^{13}$ NMR analysis the product was identified as N-[2-hydroxy-3-(maltodextrin 10)-glycosylpropyl], N,N-dimethyl-3-methacrylamidopropylammonium chloride (MW~1900), hereinafter referred to as DMAPMA-maltodextrin 10-glycoside, having the structure:

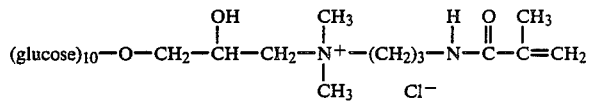

EXAMPLE 6

This example illustrates the preparation of N-[2-hydroxy-3-glucoglycosyl-propyl]-4-vinylpyridinium chloride.

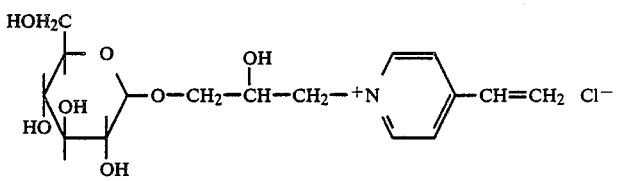

A total of 15 g dry basis (0.034 moles) of 3-chloro-2-hydoxypropyl glucoglycoside was dissolved in 15 g of distilled water in a 100 ml. round bottom flask. Six ml (0.056 moles) of 4-vinyl pyridine was added slowly with cooling. The mixture was heated to 60° C. and stirred for 16 hours. The mixture was recovered as in Example 3. The product was a dark red, tacky solid. No organic chlorine was detected indicating the reaction was quantitative. C$^{13}$ NMR analysis showed the presence of the vinyl group at 118.5 and 135.2 ppm, however, the product was shown to contain some polymeric products.

EXAMPLE 7

This example illustrates the preparation of N-[2-hydroxy-3-glucoglycosyl-propyl], N-methyldiallylammonium chloride.

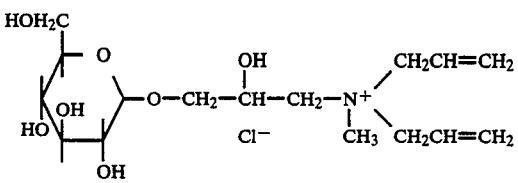

A total of 22.1 g dry basis (0.08 moles) of 3-chloro-2-hydroxypropyl glucoglycoside was dissolved in 10 g of water and reacted with 12.0 g (0.10 moles) of N-methyldiallylamine by the procedure described in Example 3. The monomer, hereinafter referred to as MDAA-glucoglycoside was recovered by precipitation in acetone then dried in a vacuum dessicator. The monomer contained very low levels of organic chlorine indicating that the reaction was almost quantitative.

EXAMPLE 8

This example illustrates the preparation of N-[2-hydroxy-3-glucoglycosyl-propyl], N-isopropyl, 3-methacrylamidopropylammonium chloride.

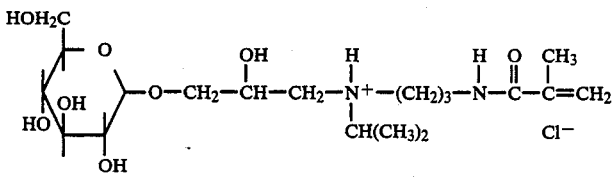

The monomer, referred to as IPAPMA-glucoglycoside was prepared as in Example 6 employing 19.0 g (0.10 moles) of N-isopropylaminopropyl methacrylamide. This monomer was also recovered in almost a quantitative yield.

EXAMPLE 9

This example illustrates the preparation of an ethynylically unsaturated cationic glycoside monomer.

A total of 12.4 g dry basis (0.045 moles) of 3-chloro-2-hydroxypropyl glucoglycoside was dissolved in 15 g of water and reacted with 2.5 g (0.045 moles) of propargylamine at 60° C. in the presence of 4 drops of 2,4,6-trimethylpyridine. After 5.5 hours a second equivalent portion of glycoside in water was added with an additional 5.8 g of 2,4,6-trimethylpyridine. The reaction continued for an additional 15 hours at 60° C. The monomer was recovered by precipitation in acetone in about a 55% yield based on chlorine analysis for a diglycoside product.

EXAMPLE 10

This example illustrates the solution homopolymerization of DMAPMA-glucoglycoside.

A total of 7.0 grams dry basis of DMAPMA-glucoglycoside and 12.0 grams of degassed water were added to a three-necked round bottom flask equipped with a mechanical stirrer, addition funnel and nitrogen source. Ammonium persulfate (0.070 g. in 4 ml. of water) was added in four increments over a period of two hours. The 30% solids solution was then heated to 70° C. and stirred for 6 hours to yield a viscous polymer product.

In addition to the observed viscosity of the polymer, polymerization was further verified by the clay flocculation test. The DMAPMA-glucogycoside did not flocculate clay, however, the cationic homopolymer prepared had a clay flocculation time of 56.5 seconds.

A 79% solids solution containing 1% ammonium persulfate based on the monomer was homopolymerized in a closed vessel under similar conditions to yield a gel with strong water retention properties.

EXAMPLE 11

This example illustrates the solution homopolymerization of DMAPMA-maltodextrin 10-glycoside.

A total of 4 parts (dry basis) of DMAPMA-maltodextrin 10-glycoside, 6 parts of degassed water and 4 parts 1% ammonium persulfate were added to a vessel and sealed under nitrogen. The solution was heated to 80° C. and allowed to react for 72 hours to yield a viscous polymer solution. A solution of the polymer had a clay flocculation time of 87 seconds.

EXAMLE 12

This example illustrates the solution homopolymerizations of MDAA-glucoglycoside and IPAPMA-glucoglycoside.

The glycoside monomers prepared in Examples 7 and 8 were solution homopolymerized as described in Example 11 at 70° C. for 1 hour. Both homopolymers were clear, slightly viscous, and smooth in texture. The MDAA-glucoglycoside homopolymer had a clay flocculation time of 78.5 seconds. The IPAPMA-glucoglycoside homopolymer had a clay flocculation time of 53.8 seconds.

EXAMPLE 13

This example illustrates the water-in-oil emulsion homopolymerization of DMAPMA-glucoglycoside.

To a 100 ml. three-necked round bottom flask equipped with stirring apparatus, condensor, addition funnel and nitrogen source was added 7.0 g. (dry basis) of DMAPMA-glucoglycoside and 6.0 g. of degassed water. A total of 7.0 g of Isopar M (branched-chain isoparaffinic oil obtained from Exxon Corporation), and 1.86 g. Tween 85 and 0.47 g. Span 80 (surfactants obtained from Imperial Chemical Industries) were slowly added with rapid stirring to form an emulsion. After the temperature of the emulsion was raised to 70° C. a total of 0.02 ml of Lupersol 11 (a 75% by weight solution of t-butyl peroxypivalate in 0.2M n-decane obtained from Pennwalt Corporation) which was dissolved in 2 ml. of Isopar M was added in three increments over three hours. The polymerization was continued for an additional three hours then stopped by the addition of 5 drops of 1% monomethyl ether hydroquinone in ethanol. When inverted in water the polymer had a clay flocculation time of 41 seconds. A 1% solution of the polymer had a Brookfield viscosity of 1000 cps. (Spindle #5 at 20 rpm).

EXAMPLE 14

This example illustrates the solution copolymerization of DMAPMA-glucoglycoside and acrylamide.

Employing a reaction apparatus similar to that described in Example 7, 6.63 g. dry basis (0.015 moles) of the glycoside monomer and 10.25 g. (0.15 moles) of acrylamide were dissolved in 60 g. of degassed water. After the solution was heated to 65° C., 0.02 g. of 2,2-azobis (2-amidinopropane)hydrochloride in 3 ml of water was added in three increments over a period of three hours. The reaction was stopped after a total of six hours by the addition of 1% monoethyl ether hydroquinone ethanol solution. The viscous solution of the cationic 1:10 molar ratio DMAPMA-glycoglycoside:acrylamide copolymer was light brown. A similar copolymer was prepared in a 2:10 molar ratio. A mixture of DMAPMA-glycoglycoside and acrylamide did not flocculate clay, however, the solution copolymers prepared had clay flocculation times of 45 to 47 seconds.

Zeta potential analysis of the copolymer showed it to be cationic, confirming that copolymerization occurred. The polymer had a poor clay flocculation time (>200 seconds) which was probably due to the relatively low molecular weight of the copolymer produced.

EXAMPLE 17

This example illustrates the preparation of water-in-oil emulsion copolymers and terpolymers of DMAPMA-glucoglycoside, DMAPMA-maltodextrin 10-glycoside, and acrylamide.

Employing an apparatus and procedure similar to that described in Example 13, the comonomers were dissolved in degassed water, formed into an emulsion, then heated to a temperature of 65° C. To each emulsion 0.03 g. of Lupersol 11 in 2 ml. of Isopar M was added in three increments over three hours. Each reaction, complete after 5 hours, was stopped with 5 drops of a 1% monomethyl ether hydroquinone ethanol solution. The reaction data is given in Table I.

TABLE I

Copolymerization of DMAPMA-Glucoglycoside:DMAPMA-Maltodextrin 10-glycoside:Acrylamide
EMULSION PREPARATION

| Polymer | A | B | C | D | E | F |
|---|---|---|---|---|---|---|
| Molar Ratio* | 1:0:10 | 2:0:10 | 1:0.115:10 | 1:0.23:10 | 1:0.47:10 | 0:1:21.45 |
| Ingredients: | | | | | | |
| DMAPMA-glucoglycoside (D.B.) (g) | 4.64 | 6.96 | 4.64 | 4.64 | 3.71 | 0 |
| DMAPMA-Maltodextrin 10-glycoside (D.B) (g) | 0 | 0 | 2.32 | 4.64 | 7.42 | 7.42 |
| Acrylamide (g) | 7.46 | 5.60 | 7.46 | 7.46 | 5.97 | 5.97 |
| Water (g) | 15 | 15 | 25 | 25 | 25 | 15 |
| Isopar M (g) | 16 | 16 | 25 | 25 | 25 | 15 |
| Tween 85 (g) | 3.72 | 3.72 | 3.72 | 3.72 | 2.97 | 2.97 |
| Span 80 (g) | 0.94 | 0.94 | 0.92 | 0.92 | 0.74 | 0.74 |
| Data: | | | | | | |
| Clay flocculation (sec.) | 19.0 | 27.0 | 36.0 | 50.2 | 22.6 | 52.7 |
| Brookfield Viscosity (cps)** | 5,680 | 1,200 | 18,250 | 10,600 | 5,800 | Watery |
| Spindle # | 5 | 4 | 6 | 6 | 5 | — |

*Molar ratio of DMAPMA-glucoglycoside:DMAPMA-maltodextrin 10-glycoside:acrylamide.
**1% solids at 20 rpm.

EXAMPLE 15

A 2.8:10 molar ratio solution copolymer of DMAPMA-maltodextrin 10-glycoside:acrylamide was prepared as in Example 11. A viscous solution was obtained after a reaction time of 6 hours. The copolymer had a clay flocculation time of 74 seconds.

EXAMPLE 16

A solution copolymer of acrylamide and the diglycoside propargyl monomer of Example 9 was prepared as in Example 11 with 4 parts of the cationic monomer (dry basis), 4.5 parts of degassed water, 1 part acrylamide, and 4 parts 1% ammonium persulfate. The reaction was conducted at 75° C. for 1 hour resulting in a slightly viscous solution. The solution was cooled to room temperature then dialyzed in order to recover only copolymers having a molecular weight greater than 1,000.

It was noted that inverted solutions of the terpolymers containing the maltodextrin 10-glycoside monomer were smooth in contrast to the usual cohesiveness exhibited by cationic copolymers.

EXAMPLE 18

This example illustrates the preparation of amphoteric terpolymers of DMAPMA-glucoglycoside: acrylamide: acrylic acid having a positive, negative, or neutral overall charge.

Employing an apparatus as described in Example 13, a solution of acrylic acid in degassed water was adjusted to a pH of 4 to 7 with 50% potassium hydroxide with cooling prior to adding the glycoside and acrylamide. The terpolymers were then emulsified and polymerized employing the reaction conditions of Example 17. The reaction data is given in Table II.

TABLE II

Polymerization of DMAPMA-glucoglycoside:Acrylamide:Acrylic Acid
EMULSION PREPARATION

| Polymer | G | H | I | J | K | L | M | N | O |
|---|---|---|---|---|---|---|---|---|---|
| Molar ratio* | 1.25: 4.65: | 1.25: 4.65: | 2.5: 2.1: | 1:4:1 | 0.5:8:3 | 0.5:8:3 | 0.5:9:3 | 0.5:10:4 | 1:10:4 |

TABLE II-continued

Polymerization of DMAPMA-glucoglycoside:Acrylamide:Acrylic Acid
EMULSION PREPARATION

| Polymer | G | H | I | J | K | L | M | N | O |
|---|---|---|---|---|---|---|---|---|---|
| | 1 | 1 | 1 | | | | | | |
| Overall Charge | + | + | + | neutral | − | − | − | − | − |
| pH | 7 | 4 | 4 | 4 | 4 | 4 | 7 | 7 | 7 |
| Ingredients: | | | | | | | | | |
| DMAPMA-glucoglycoside (D.B.) (g) | 7.89 | 7.54 | 12.26 | 5.52 | 1.41 | 1.41 | 1.41 | 1.41 | 2.81 |
| Acrylamide (g) | 4.89 | 4.57 | 1.65 | 3.55 | 3.60 | 3.60 | 4.08 | 4.50 | 4.50 |
| Acrylic Acid (g) | 1.03 | 0.98 | 0.80 | 0.90 | 1.38 | 1.38 | 1.36 | 1.84 | 1.84 |
| Water (g) | 14 | 14 | 14 | 10 | 10 | 10 | 10 | 10 | 10 |
| Isopar M (g) | 16 | 16 | 16 | 7.5 | 8 | 8 | 8 | 8 | 8 |
| Tween 85 (g) | 3.72 | 3.72 | 3.72 | 0.62 | 0.62 | 2.48 | 2.48 | 2.48 | 2.48 |
| Span 80 (g) | 0.94 | 0.94 | 0.94 | 2.48 | 2.48 | 0.62 | 0.62 | 0.62 | 0.62 |
| Clay flocculation (sec.) | 26.6 | 28.6 | 35.6 | — | — | — | — | — | — |

*Molar ratio of DMAPMA-glucoglycoside:acrylamide:acrylic acid

EXAMPLE 19

The emulsion terpolymers G–L described above were evaluated as drainage aids in an acid system. The results are given in Table III.

TABLE III

DRAINAGE IN AN ACID SYSTEM

| | Drainage Rate (ml/sec) in Presence of 3.3% Alum at Treatment Levels: | | % of Control | |
|---|---|---|---|---|
| Polymer | 0.1% | 0.2% | 0.1% | 0.2% |
| Blank | 39.5 | 39.5 | — | — |
| Control* | 62.2 | 88.2 | — | — |
| G | 79.0 | 125.9 | 127.0 | 142.4 |
| H | 82.8 | 107.2 | 133.1 | 121.4 |
| I | 64.5 | 80.3 | 103.8 | 91.0 |
| J | 66.1 | 82.8 | 106.3 | 93.8 |
| K | 43.6 | 47.2 | 70.2 | 53.5 |
| L | 94.5 | 131.2 | 152.0 | 148.0 |

*Phosphorylated diethylaminoethyl ether of waxy maize starch.

The results show that amphoteric terpolymers containing DMAPMA-glucoglycoside were effective drainage aids in an acid system and in many cases performed better than the control.

EXAMPLE 20

Cationic emulsion polymers were evaluated as drainage aids in a neutral system. The results are given in Table IV.

TABLE IV

DRAINAGE IN A NEUTRAL SYSTEM

| | Drainage Rate (ml/sec) at Treatment Levels: | | | % of Control | | |
|---|---|---|---|---|---|---|
| Polymer | 0.1% | 0.2% | 0.4% | 0.1% | 0.2% | 0.4% |
| Blank | 32.0 | 32.0 | 32.0 | — | — | — |
| Control* | 38.1 | 49.9 | 74.1 | — | — | — |
| DMAPMA-glucoglycoside homopolymer** | 56.6 | 99.2 | 109.1 | 148.6 | 198.8 | 147.3 |
| A | 59.9 | 101.7 | 127.7 | 157.1 | 203.8 | 172.4 |
| B | 73.2 | 93.0 | 114.8 | 192.1 | 186.4 | 155.0 |
| Blank | 39.3 | 39.2 | — | — | — | — |
| Control* | 38.8 | 50.2 | — | — | — | — |
| G | 37.7 | 47.1 | — | 97.0 | 93.7 | — |
| H | 42.9 | 46.7 | — | 110.4 | 93.0 | — |
| I | 43.8 | 59.0 | — | 112.8 | 117.4 | — |

*Diethylaminoethyl ether of waxy maize starch.
**Emulsion homopolymer of Example 13.

The results show that the cationic DMAPMA-glucoglycoside homopolymer and copolymers with acrylamide were better than the control in a neutral drainage system. Amphoteric terpolymers having an overall positive charge which contained the glycoside monomer also performed as well or better than the control.

EXAMPLE 21

This example illustrates the preparation of 2-chloroethyl glucoglycoside.

To an apparatus described in Example 1 was added 80 g. dextrose, 147.48 ml. (2.20 moles) 2-chloroethanol, and 20 g. Dowex 50W-X8 in H+ form. With stirring the mixture was heated to 90° C. until the dextrose dissolved. The reaction was then cooled and held to 60° C. for 16 hours. The resin was removed and the product recovered as in Example 1. The ethyl glycoside contained 11.59% organic chloride instead of 14.64% (theoretical). $C^{13}$NMR spectral analysis indicated the absence of signals corresponding to the hemi-acetal form of the reducing carbon atom.

EXAMPLE 22

This example illustrates the preparation of N-[2-glucoglycosylethyl], N-diallyamine.

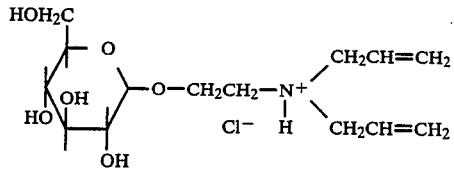

A total of 12.1 g. dry basis of 2-chloroethyl glucoglycoside of Example 21 was dissolved in 10 g. of water and reacted with 4.85 g. diallyl amine according to the procedure of Example 3 with the exception that the reaction mixture did not contain monoethyl ether hydroquinone and the reaction was conducted at 60° C. instead of 40° C. Based on chlorine analysis, the monomer, referred to as DAA-glucoglycoside was not recovered in quantitative yield.

EXAMPLE 23

This example illustrates the solution polymerization of DAA-glucoglycoside and acrylamide.

A total of 1.6 g. of DAA-glucoglycoside (65% solids), 0.6 g. acrylamide, 1.0 g. degassed water and 0.015 g. potassium pesulfate were charged in a vessel and sealed under nitrogen. The solution was heated to 73° C. and held for 1.5 hours to yield a viscous polymer solution. The solution was cooled to room temperature then dialyzed in order to recover only polymers having a moleclar weight greater than 1,000. C$^{13}$ NMR analysis showed the presence of α- and β-glycoside carbon linkages at 98.4 and 102.9 ppm and the absence of reducing carbon atom signals. Signals between 61.2 and 76.2 ppm were present corresponding to the carbohydrate moiety and signals at 30.3, 36.0, 43.8, 52.0, and 55.5 ppm were assigned to pyrrolidino and methylene carbon atoms. A solution of the polymer at pH=4.6 had a clay flocculation time of 43.2 seconds.

EXAMPLE 24

This example illustrates the preparation of a graft copolymer of a polysaccharide and a cationic glycoside monomer of the present invention.

To a 100 ml. three-necked round bottom flask equipped with stirring apparatus, condensor, addition funnel and nitrogen source was added 7.0 g. (dry basis) of DMAPMA-glucoglycoside and 5.0 g. of degassed water. A total of 25.0 g. Isopar M, 1.86 g. Tween 85, 0.47 g. Span 80, and 10.0 g. (as is) of granular waxy maize corn starch (acid hydrolyzed to a final water fluidity of 85) were slowly added with rapid stirring to form a suspension. After the temperature of the suspension was raised to 70° C., a total of 0.1 ml. of Lupersol 11 which was dissolved in 2 ml. of Isopar M was added in three increments over three hours. The graft copolymerization was continued for an additional three hours then stopped by the addition of 5 drops of 1% monomethyl ether hydroquinone in ethanol. The starch graft copolymer was filtered, washed with a 50:50 ethanol: water mixture and air dried. The graft copolymer had a nitrogen content of 0.17% (dry basis) corresponding to a 6.2% grafting efficiency. The graft copolymer had a clay flocculation time of 168 seconds.

EXAMPLE 25

The reaction of Example 24 was repeated with the exception that the polysaccharide base employed was a derivatized starch ether base having unsaturated substituents prepared according to the following procedure:

A total of 100 parts of acid hydrolyzed waxy starch (water fluidity 85) was slurried in an aqueous solution of 1.5 parts sodium hydroxide and 25 parts sodium sulfate in 150 parts water. A total of 0.2 parts allylglycidyl ether was added to the starch slurry. The mixture was agitated at 40° C. for 16 hours and the pH was lowered to 5.5 by the addition of 9.3% aqueous hydrochloric acid. The starch ether derivative was recovered by filtration, was three times with water and air-dried.

The graft copolymer of this example had an improved grafting efficiency (32.4% based on a nitrogen content of 0.88%) in comparison to the graft copolymer of Example 24. Clay flocculation of the sample was also improved (118 seconds).

We claim:
1. A cationic glycoside monomer having the structure:

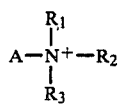

wherein A is (saccharide)$_n$—O—B and (saccharide)-$_n$—O— represents a mono- or polysaccharide of no more than 20 saccharide units, where O is attached to a glycosidic carbon atom in the terminal saccharide ring of (saccharide)$_n$, B is —CH$_2$CH(OH)CH$_2$— or —CH$_2$CH$_2$—, and n is 1 to 20;

wherein R$_1$ is selected from the group consisting of H; C$_1$-C$_6$ alkyl; C$_2$-C$_6$ alkenyl or alkynyl; benzyl; and A;

R$_2$ is selected from the group consisting of H; C$_1$-C$_6$ alkyl; C$_2$-C$_6$ alkenyl or alkynyl; benzyl; and A;

R$_3$ is —Z—C(Y)=CH$_2$ or —Z—C≡CH wherein Y is H or C$_1$-C$_3$ alkyl and z is —Q—P— with Q being an alkyl group which divalently joins the cationic nitrogen atom with P wherein P is a polar activating group juxtapositional to the unsaturated group and is selected from the group consisting of

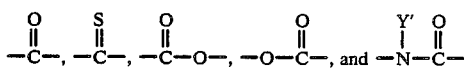

wherein Y' is H or C$_1$-C$_3$ alkyl; or R$_3$ is C$_2$-C$_7$ alkenyl or alkynyl with the proviso that R$_1$ and R$_2$ are independently H, A, or a hydocarbon group which together with R$_3$ contain a maximum of 7 carbon atoms; or R$_2$ and R$_3$ together with the nitrogen atom to which they are bonded form a 5 to 6 member saturated heterocyclic ring substituted with a group represented by the formula —C(Y)=CH$_2$ or —C≡CH;

wherein R$_4$ and R$_5$ together with the nitrogen atom to which they are bonded form a 5 or 6 member unsaturated heterocyclic ring substituted with a group represented by the formula —C(Y)=CH$_2$ or —C≡CH; and M is an anion.

2. The glycoside monomer of claim 1, wherein the saccharide unit is glucose and n is 1 and wherein R$_1$ is H, methyl, or A, R$_2$ is —CH$_2$CH=CH$_2$, and R$_3$ is —CH$_2$CH=CH$_2$; or R$_1$ is H or A, R$_2$ is H or A, and R$_3$ is —CH$_2$C≡CH.

3. The glycoside monomer of claim 1, wherein R$_3$ is —Z—C(Y)=CH$_2$ or —Z—C≡CH and Q is C$_1$-C$_3$ alkyl.

4. The glycoside monomer of claim 3 having the structure:

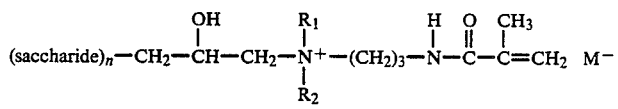

wherein R$_1$ and R$_2$ are independently H or C$_1$-C$_6$ alkyl.

5. The glycoside monomer of claim 4, wherein the saccharide unit is glucose, n is 1 to 10, R$_1$ is H or methyl, and R$_2$ is methyl or isopropyl.

6. The glycoside monomer of claim 1, wherein B is —CH$_2$CH(OH)CH$_2$—.

7. The glycoside monomer of claim 6, wherein R$_2$ and R$_3$ together with the nitrogen atom to which they are bonded form a 5 or 6 member saturated heterocyclic ring substituted with a group represented by the formula —C(Y)=CH$_2$ or —C≡CH; R$_4$ and R$_5$ together with the nitrogen atom to which they are bonded form a 5 or 6 member unsaturated heterocyclic ring substituted with a group represented by the formula —C(Y)=CH$_2$ or —C≡CH; or wherein R$_3$ is C$_2$-C$_7$ alkenyl or alkynyl, —Z—C(Y)=CH$_2$ or —Z—C≡CH and R$_1$ or R$_2$ is C$_2$-C$_6$ alkenyl or alkynyl.

8. A homopolymer represented by the formula (Mer)$_n$ wherein Mer represents the cationic glycoside monomer of claim 7 with n being greater than 1.

9. A copolymer prepared from an ethylenically unsaturated comonomer and the cationic glycoside monomer of claim 7, wherein said comonomer is selected from the group consisting of a styrene; acrylic acid, alkyl or hydroxyalkyl substituted acrylic acid, or an alkali metal, alkaline earth metal or ammonium salt thereof or an ester thereof with a C$_1$-C$_{18}$ alcohol; a dialkylaminoalkyl ester of acrylic acid or methacrylic acid; isoprene; acrylamide, alkyl substituted, N-alkyl substituted or an N-alkanol substituted compound thereof; acrylonitrile; methacrylonitrile; butadiene; a vinyl compound; a halogenated vinyl compound, an unsaturated vinylic acid or a salt or ester thereof; an allyl ester of a saturated aliphatic monocarboxylic acid; ethylene; propylene; diallyl maleate; and diallyl phthalate.

10. A polymer comprising more than one unit of a cationic glycoside monomer wherein the polymer is (A) a homopolymer prepared by homopolymerizing said cationic glycoside monomer or (B) a copolymer prepare from an ethylenically unsaturated comonomer and said cationic glycoside monomer; said cationic glycoside monomer having the structure

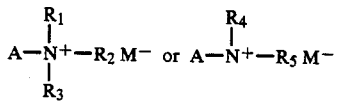

wherein A is (saccharide)$_n$—O—CH$_2$CH$_2$— and (saccharide)$_n$—O— represents a mono- or polysaccharide of no more than 20 saccharide units, where O is attached to a glycosidic carbon atom in the terminal saccharide ring of (saccharide)$_n$, and n is 1 to 20;

wherein R$_1$ is selected from the group consisting of H; C$_1$-C$_6$ alkyl; C$_2$-C$_6$ alkenyl or alkynyl; benzyl; and A;

R$_2$ is selected from the group consisting of H; C$_1$-C$_6$ alkyl; C$_2$-C$_6$ alkenyl or alkynyl; benzyl; and A;

R$_3$ is selected from the group consisting of C$_2$-C$_7$ alkenyl or alkynyl or R$_3$ is represented by the formula —Z—C(Y)=CH$_2$ or —Z—C≡CH wherein Y is H or C$_1$-C$_3$ alkyl and Z is —Q—P— with Q being an alkyl group which divalently joins the cationic nitrogen atom with P wherein P is a polar activating group juxtapositional to the unsaturated group and is selected from the group consisting of

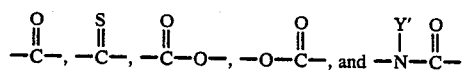

wherein Y' is H or C$_1$-C$_3$ alkyl; or R$_2$ and R$_3$ together with the nitrogen atom to which they are bonded form a 5 or 6 member saturated hetercyclic ring substituted with a group represented by the formula —C(Y)=CH$_2$ or —C≡CH;

wherein R$_4$ and R$_5$ together with the nitrogen atom to which they are bonded form a 5 or 6 member unsaturated heterocyclic ring substituted with a group represented by the formula —C(Y)=CH$_2$ or —C≡CH; and M is an anion; and wherein said ethylenically unsaturated comonomer is selected from the group consisting of a styrene; acrylic acid, alkyl or hydroxyalkyl substituted acrylic acid, or an alkali metal, alkaline earth metal or ammonium salt thereof or an ester thereof with a C$_1$-C$_{18}$ alcohol; a dialkylaminoalkyl ester of acrylic acid or methacrylic acid; isoprene; acrylamide, alkyl substituted, N-alkyl substituted or an N-alkanol substituted compound thereof; acrylonitrile; methacrylonitrile; butadiene; a vinyl compound; a halogenated vinyl compound, an unsaturated vinylic acid or a salt or ester thereof; an allyl ester of a saturated aliphatic monocarboxylic acid; ethylene; propylene; diallyl maleate; and diallyl phthalate.

11. A method of preparing a polymer having a synthetic polymer backbone and recurring saccharide side chain units comprising the step of homopolymerizing a cationic glycoside monomer or copolymerizing said cationic glycoside monomer with an ethylenically unsaturated comonomer; said cationic glycoside monomer having the structure

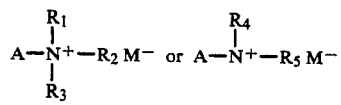

wherein A is (saccharide)$_n$—O—B— and (saccharide)$_n$—O— represents a mono- or polysaccharide of no more than 20 saccharide units, where O is attached to a glycosidic carbon atom in the terminal saccharide ring of (saccharide)$_n$, B is —CH$_2$CH(OH)CH$_2$— or —CH$_2$CH$_2$—, and n is 1 to 20;

wherein R$_1$ is selected from the group consisting of H; C$_1$-C$_6$ alkyl; C$_2$-C$_6$ alkenyl or alkynyl; benzyl; and A;

R$_2$ is selected from the group consisting of H; C$_1$-C$_6$ alkyl; C$_2$-C$_6$ alkenyl or alkynyl; benzyl; and A;

R$_3$ is selected from the group consisting of C$_2$-C$_7$ alkenyl or alkynyl or R$_3$ is represented by the formula —Z—C(Y)=CH$_2$ or —Z—C≡CH wherein Y is H or C$_{1-C3}$ alkyl and Z is —Q—P— with Q being an alkyl group which divalently joins the cationic nitrogen atom with P wherein P is a polar activating group juxtapositional to the unsaturated group and is selected from the group consisting of

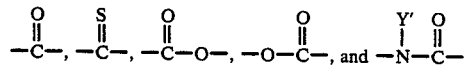

wherein Y' is H or C$_1$-C$_3$ alkyl; or R$_2$ and R$_3$ together with the nitrogen atom to which they are bonded form a 5 or 6 member saturated hetercyclic ring substituted with a group represented by the formula —C(Y)=CH$_2$ or —C≡CH;

wherein R$_4$ and R$_5$ together with the nitrogen atom to which they are bonded form a 5 or 6 member unsaturated heterocyclic ring substituted with a group represented by the formula $-C(Y)=CH_2$ or $-C\equiv CH$; and M is an anion; and wherein said ethylenically unsaturated comonomer is selected from the group consisting of a styrene; acrylic acid, alkyl or hydroxyalkyl substituted acrylic acid, or an alkali metal, alkaline earth metal or ammonium salt thereof or an ester thereof with a $C_1$-$C_{18}$ alcohol; a dialkylaminoalkyl ester of acrylic acid or methacrylic acid; isoprene; acrylamide, alkyl substituted, N-alkyl substituted or an N-alkanol substituted compound thereof; acrylonitrile; methacrylonitrile; butadiene; a vinyl compound; a halogenated vinyl compound, an unsaturated vinylic acid or a salt or ester thereof; an allyl ester of a saturated aliphatic monocarboxylic acid; ethylene; propylene; diallyl maleate; and diallyl phthalate.

12. A polysaccharide-g-copolymer represented by the structure

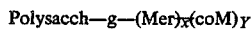

wherein Polysacch— represents a polysaccharide molecule; Mer represents a cationic glycoside monomer having the structure:

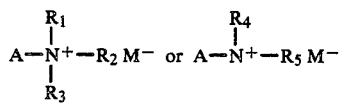

wherein A is (saccharide)$_n$—O—B— and (saccharide)$_n$—O— represents a mono- or polysaccharide of no more than 20 saccharide units, where O is attached to a glycosidic carbon atom in the terminal saccharide ring of (saccharide)$_n$, B is —CH$_2$CH(OH)CH$_2$— or —CH$_2$CH$_2$—, and n is 1 to 20;

wherein $R_1$ is selected from the group consisting of H; $C_1$-$C_6$ alkyl; $C_2$-$C_6$ alkenyl or alkynyl; benzyl; and A;

$R_2$ is selected from the group consisting of H; $C_1$-$C_6$ alkyl; $C_2$-$C_6$ alkenyl or alkynyl; and A;

$R_3$ is selected from the group consisting of $C_2$-$C_7$ alkenyl or alkynyl or $R_3$ is represented by the formula $-Z-C(Y)=CH_2$ or $-Z-C\equiv CH$ wherein Y is H or $C_1$-$C_3$ alkyl and Z is —Q—P— with Q being an alkyl group which divalently joins the cationic nitrogen atom with P wherein P is a polar activating group juxtapositional to the unsaturated group and is selected from the group consisting of

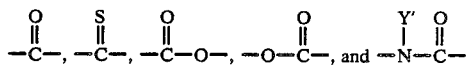

wherein Y' is H or $C_1$-$C_3$ alkyl; or $R_2$ and $R_3$ together with the nitrogen atom to which they are bonded form a 5 or 6 member saturated hetercyclic ring substituted with a group represented by the formula $-C(Y)=CH_2$ or $-C\equiv CH$;

wherein $R_4$ and $R_5$ together with the nitrogen atom to which they are bonded form a 5 or 6 member unsaturated heterocyclic ring substituted with a group represented by the formula $-C(Y)=CH_2$ and $-C\equiv CH$; and M is an anion; coM represents a copolymerizable comonomer; x and y are integers wherein x is at least 1 and x+y≧2.

13. The polysaccharide-g-copolymer of claim 12 wherein the polysaccharide is a starch or starch conversion product or a derivative thereof, cellulose or cellulose derivative, or a plant gum.

14. The polysaccharide-g-copolymer of claim 13 wherein the polysaccharide is a starch derivative wherein the derivative contains an unsaturated group.

15. The polysaccharide-g-copolymer of claim 14 wherein the polysaccharide is the derivative of a converted starch.

16. The polysaccharide-g-copolymer of claim 12 wherein Y is O.

* * * * *

UNITED STATES PATENT AND TRADEMARK OFFICE
CERTIFICATE OF CORRECTION

PATENT NO. : 4,719,272

DATED : January 12, 1988

INVENTOR(S) : Tsai, et al.

It is certified that error appears in the above-identified patent and that said Letters Patent are hereby corrected as shown below:

Column 4, line 27 and 28, last word in line 27 should read -- present --. Column 8, line 54, in the structure, "Polyssacch" should read -- Polysacch --; and in line 68, the formula should read $x + y \geq 2$. Column 9, line 7, "practioner" should read -- practitioner --. Column 10, line 44 and 45, last word in line 44 should read -- recovered --. Column 11, line 64, last word should read -- pyrrolidinone --. Column 14, line 49, "condensor" should read -- condenser --. Column 15, line 7, "10.25" should read -- 10.65 --. Column 18, line 68, "viscious" should read -- viscous --. Column 19, line 18, "condensor" should read -- condenser --; and in line 51, "was" should read -- washed --. Column 20, lines 1-5, the structure should include -- $M^-$ or -- adjacent to "$R_2$" and be followed by the structure -- $A - \overset{\overset{R_4}{|}}{N^+} - R_5 \ M^-$ --; and in line 48 the formula reading "$-CH_2C = CH$" should read -- $-CH_2CH = CH_2$ --.

Column 21, line 68, "hetercyclic" should read -- heterocyclic --. Column 22, line 64, "hetercyclic" should read -- heterocyclic --. Column 23, line 1, "hetercyclic" should read -- heterocyclic --. Column 24, line 22, "hetercyclic" should read -- heterocyclic --; and line 27, "hetercyclic" should read -- heterocyclic --.

Signed and Sealed this

Second Day of August, 1988

Attest:

DONALD J. QUIGG

Attesting Officer

Commissioner of Patents and Trademarks